US00PP32360P2

(12) United States Plant Patent
Smith

(10) Patent No.: US PP32,360 P2
(45) Date of Patent: Oct. 20, 2020

(54) ***VERONICA* PLANT NAMED 'PINK PASSION'**

(50) Latin Name: *Veronica spicata*
Varietal Denomination: PINK PASSION

(71) Applicant: Christopher Smith, Bromsgrove (GB)

(72) Inventor: Christopher Smith, Bromsgrove (GB)

( * ) Notice: Subject to any disclaimer, the term of this patent is extended or adjusted under 35 U.S.C. 154(b) by 0 days.

(21) Appl. No.: 16/501,769

(22) Filed: Jun. 4, 2019

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./251, 263.1, 226
CPC ... A01H 5/02; A01H 5/00; A01H 6/68; A01H 6/50; A01H 5/08; A01H 5/12; A01H 6/88
See application file for complete search history.

(56) References Cited

PUBLICATIONS

Wyevale Nurseries 2018 Catablogue, retrieved on Feb. 10, 2020, retrieved from the Internet at http://www.wyevalenurseries.co.uk/media_files/file/Wyevale%20Nurseries%202018%20Catalogue.pdf, pp. 1-2,83,111. (Year: 2018).*

* cited by examiner

*Primary Examiner* — June Hwu
(74) *Attorney, Agent, or Firm* — Cassandra Bright

(57) ABSTRACT

A new and distinct *Veronica* cultivar named 'PINK PASSION' is disclosed, characterized by a strong pink flower color and a long, continuous flowering season. Plants are bushy with prolific branching and observed improved resistance to powdery mildew. The new variety is a *Veronica*, typically used for ornamental outdoor purposes.

2 Drawing Sheets

Latin name of the genus and species: *Veronica spicata.*
Variety denomination: 'PINK PASSION'.

The new *Veronica* cultivar was found as a spontaneous seedling near a crop of the unpatented commercial variety *Veronica spicata* 'Giles van Hees'. This new variety was discovered by the inventor Christopher Smith, in June 2015, at a nursery in Stourport-on-Severn, United Kingdom.

Asexual reproduction of the new cultivar 'PINK PASSION' was first performed at a nursery in Stourport-on-Severn, United Kingdom, in September 2015 by vegetative terminal cuttings. Subsequent propagation has shown that the unique features of this cultivar are stable and reproduced true to type in several successive generations.

SUMMARY OF THE INVENTION

The cultivar 'PINK PASSION' has not observed under all possible environmental conditions. The phenotype may vary somewhat with variations in environment such as temperature, day length and light intensity, without however, any variance in genotype.

The following traits have been repeatedly observed and are determined to be the unique characteristics of 'PINK PASSION'. These characteristics in combination distinguish 'PINK PASSION' as a new and distinct *Veronica* cultivar:

1. Strong pink flower color.
2. Plant has long and continuous flower season from late Spring to late Summer.
3. Bushy plant habit with prolific branching, particularly if pinched as a young plant.
4. In production trials, has shown resistance to powdery mildew (*Sphaerotheca* spp.) to be much better than comparable varieties.

COMPARISON TO THE PARENT VARIETY

Plants of the new cultivar are similar to plants of the parent, in most horticultural characteristics, however, plants of the new cultivar differ in the following;

1. Individual flowers are larger in the new variety than the parent.
2. Leaves are larger and darker green in the new variety than the parent.
3. New variety is more vigorous than the parent.
4. Flower is a slightly richer pink color in the new variety than in the parent.

COMPARISON TO COMMERCIAL VARIETY

Plants of the new cultivar can be compared to the unpatented commercial variety *Veronica* 'Rotfuchs'. These varieties are similar in most horticultural characteristics; however, the new cultivar differs in the following:

1. The new variety is more vigorous than this comparator.
2. Plants of the new variety have larger leaves than this comparator.
3. The new variety is a shorter plant than this comparator.
4. The new variety offers better resistance to powdery mildew than this comparator.

BRIEF DESCRIPTION OF THE PHOTOGRAPHS

Figure 1:
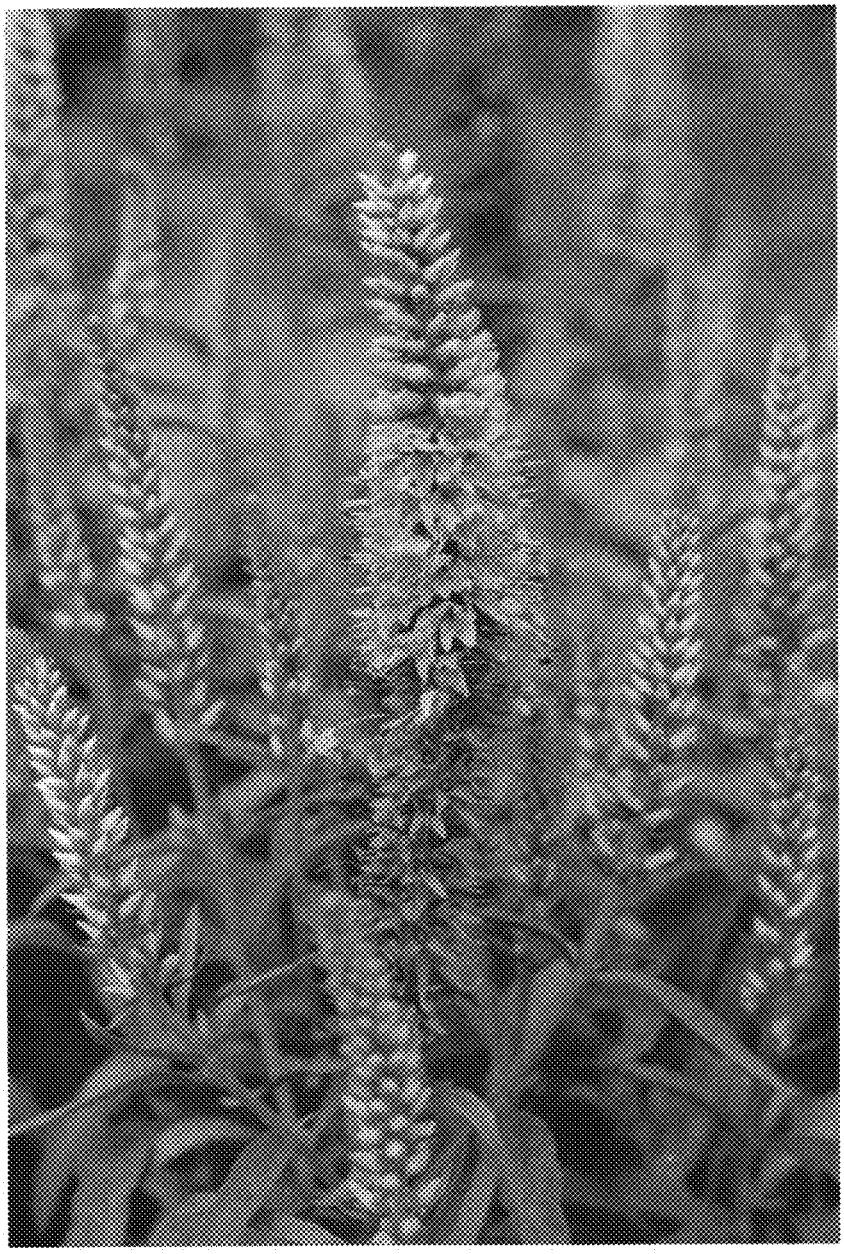

The accompanying photograph in FIG. 1 illustrates in full color inflorescence of the new variety.

Figure 2:
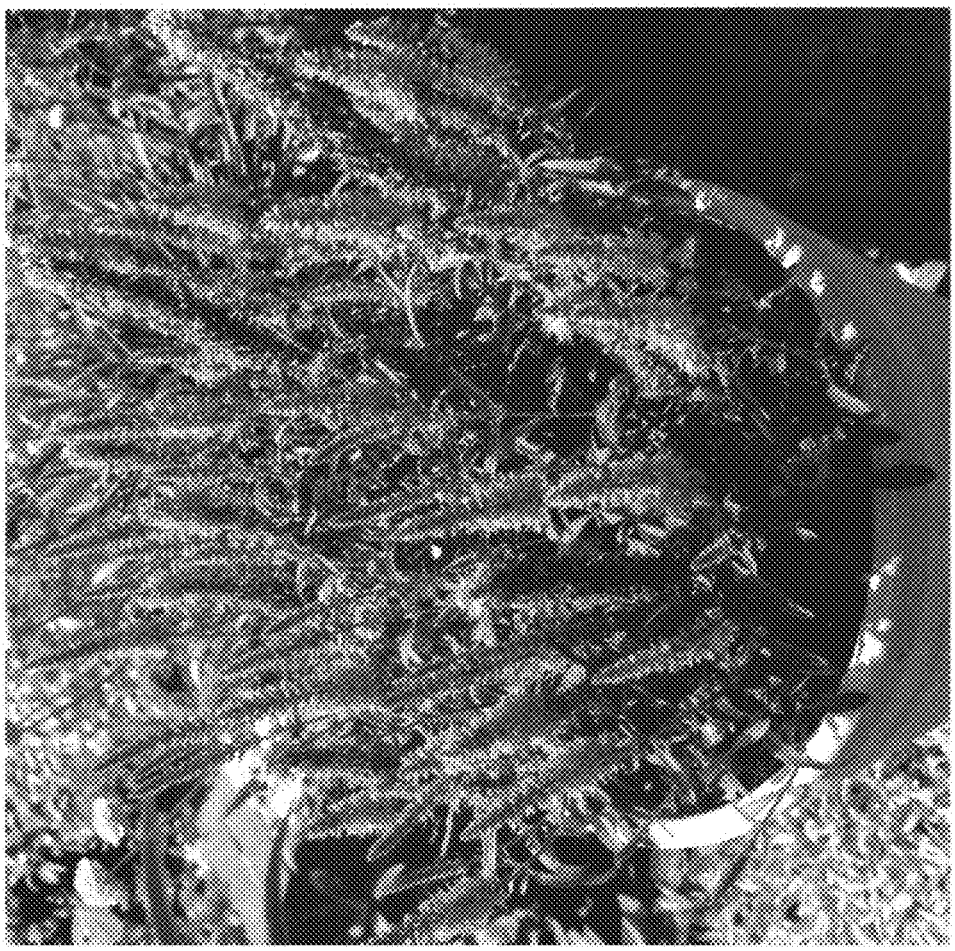

FIG. 2 illustrates a typical plant of 'PINK PASSION' grown in a greenhouse. Age of the plant photographed is approximately 12 months.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurement describe 'PINK PASSION' plants at approximately 5 months of age, grown outdoors in East Sussex, United Kingdom, between July and August. The growing temperature ranged from about 0° C. to 32° C. during the day and about - 7° C. to 25° C. night. General light conditions are bright, normal sunlight. Measurements and numerical values represent averages of typical plant types. No growth regulators were used.

Botanical classification: *Veronica spicata* 'Pink Passion'.

PROPAGATION

Time to initiate roots: About 14 days at approximately 20° C.

Root description: Fibrous. Tan to brown, not accurately measured with R.H.S. Colour Chart.

PLANT

Plant type: Flowering perennial.
Growth habit: Upright and somewhat branching.
Pot size of plant described: 25 cm.
Height: Approximately 23 to 24 cm.
Plant spread: About 32 cm.
Growth rate: Moderately vigorous.
Branching characteristics:
Length of primary lateral branches: Approximately 12 to 16 cm.
Diameter of lateral branches: Approximately 0.1 to 0.15 cm.
Texture of lateral branches: Smooth.
Internode length: About 2 cm.
Strength of stem: Rigid.
Color of lateral branches: Near RHS Yellow-Green 146C.
Aspect/angle of branches: 30° from vertical.
Number of leaves per lateral branch: Approximately 4-6.

FOLIAGE

Leaf:
- *Arrangement*.—Opposite in pairs.
- *Length*.—Approximately 4.9 cm.
- *Average width*.—Approximately 1.4 cm.
- *Shape of blade*.—Elliptic.
- *Apex*.—Obtuse.
- *Base*.—Acuminate.
- *Margin*.—Basal foliage crenate, upper foliage entire.
- *Texture of top surface*.—Sparsely pubescent.
- *Texture of bottom surface*.—Sparsely pubescent, more strongly pubescent on midrib.
- *Appearance top surface*.—Matte.
- *Appearance bottom surface*.—Matte, slightly glossy midrib.
- *Leaf internode length*.—Approximately 0.5 to 0.7 cm.
- *Color*.—Young foliage upper side: Near RHS Yellow-Green 146B. Young foliage under side: Near RHS Yellow-Green 147B. Mature foliage upper side: Near RHS Green NN137B. Mature foliage under side: Near RHS Green 137B.
- *Venation*.—Type: Pinnate. Venation color upper side: Near RHS Yellow-Green 143B. Venation color under side: Near RHS Yellow-Green 143C.

Petiole:
- *Shape*.—Flattened.
- *Length*.—1.8 to 2.0 cm. below lowest flowers.
- *Diameter*.—0.15 to 0.2 cm.
- *Pubescence*.—Finely pubescent.
- *Color*.—Near RHS Yellow-Green 146A, 146C near base.

FLOWER

Natural flowering season: Late Spring through late Summer, flowering continuously.
Days to flowering from rooted cutting: 60 days during the Spring season.
Flower longevity on plant: 6 to 8 days.
Persistent or self-cleaning: Self-cleaning.
Fragrance: None.

Bud:
- *Bud shape*.—Lanceolate.
- *Bud length*.—Approximately 0.4 cm.
- *Bud diameter*.—Approximately 0.1 cm.
- *Bud color*.—When first emerging: Between RHS Green-White 157D and White NN155C. When opening: Between RHS Red-Purple 73A and 68A.
- *Opening rate, from bud to fully open*.—3 to 7 days, depending upon weather.

Inflorescence:
- *Arrangement*.—Terminal raceme. Narrow triangular in shape.
- *Inflorescence height*.—12.5 cm from bottom of flower to tip.
- *Inflorescence width*.—2 cm.
- *Quantity of flowers per inflorescence*.—Approximately 125 to 150.
- *Typical quantity of Inflorescence per plant*.—90 to 100, with more forming.

Individual flower form: Campanulate.

Flower:
- *Diameter of entire flower*.—Approximately 0.8 cm.
- *Length of flower*.—Approximately 0.9 cm.

Petals:
- *Quantity*.—4.
- *Arrangement*.—Cruciform, fused at the base.
- *Length*.—0.6 cm.
- *Width*.—0.2 cm.
- *Shape*.—Broadly linear.
- *Apex*.—Rounded.
- *Base*.—Fused.
- *Margin*.—Entire.
- *Texture, upper and lower surfaces*.—Glabrous.
- *Appearance upper and lower surfaces*.—Matte.
- *Color*.—When opening, upper surface: Near RHS Red-Purple 67B. When opening, lower surface: Near RHS Red-Purple 67B. Fully opened, upper surface: Near RHS Red-Purple 68A. Fully opened, lower surface: Near RHS Red-Purple 67C. Fading, upper surface: Near RHS Red-Purple 67C. Fading, lower surface: Near RHS Red-Purple 67C.

*Corolla tube*.—Length: 0.3 cm. Color: Interior: Near RHS Red-Purple 68D. Exterior: Near RHS Red-Purple 67C.

Calyx/sepals:

*Shape*.—4 lobes fused at base to form a tube.

*Length*.—Total length approximately 4 mm, lobes 1-2 mm.

*Width*.—Approximately 2-3 mm.

*Texture*.—Finely pubescent.

*Color*.—RHS Green 143C.

Peduncle:

*Peduncle length*.—Approximately 0.5 to 2.0 cm.

*Peduncle diameter*.—Approximately 0.1 to 0.15 cm.

*Color*.—Between RHS Yellow-Green 144A and 144B.

*Peduncle texture*.—Finely pubescent.

Pedicels:

*Pedicel length*.—Approximately 0.25 cm.

*Pedicel diameter*.—Approximately 0.1 or less cm.

*Angle*.—Approximately 30° from attachment.

*Color*.—Between RHS Yellow-Green 144A and 144B.

*Pedicel texture*.—Finely pubescent.

Bracts:

*Shape*.—Narrow deltoid.

*Length*.—Variable, 5 to 15 mm.

*Width*.—Approximately 3-6 mm.

*Texture*.—Finely pubescent.

*Color*.—RHS Green 143C.

REPRODUCTIVE ORGANS

Androecium:

*Stamens*.—2.

*Anther shape*.—Ovoid.

*Anther length*.—Approximately 0.1 cm.

*Anther color*.—Near RHS Greyed-Purple 184A.

*Pollen quantity*.—Moderate.

*Pollen color*.—RHS Yellow 4D.

*Filament length*.—0.5 cm.

*Filament color*.—Paler than RHS Purple 75D.

Gynoecium:

*Pistil number*.—1.

*Pistil shape*.—Pistil, stigma and style are indistinct but overall shape is filiform.

*Pistil length*.—Approximately 0.8 cm.

*Style length*.—Approximately 0.3 cm

*Style color*.—Near RHS Purple N78A.

*Stigma shape*.—Globular.

*Stigma color*.—Near RHS Purple N78A.

*Ovary diameter*.—0.7 cm.

*Ovary color*.—Between RHS Greyed-Green 193A and 194D.

OTHER CHARACTERISTICS

Seeds and fruits: Not observed to date.

Disease/pest resistance: Appears to offer above average resistance to powdery mildew during production trials in England. Neither resistance nor susceptibility to normal pests of *Veronica*.

Temperature tolerance: USDA Zones 4 through 8.

What is claimed is:

1. A new and distinct *Veronica* plant named 'PINK PASSION' as herein illustrated and described.

* * * * *